United States Patent [19]
Steinbach

[11] Patent Number: 5,984,920
[45] Date of Patent: Nov. 16, 1999

[54] ROTATABLE SPHINCTEROTOME/ PAPILLOTOME AND METHOD OF USE

[75] Inventor: Jörg Steinbach, Marquartstein, Germany

[73] Assignee: Medi-Globe Corporation, Tempe, Ariz.

[21] Appl. No.: 08/853,940

[22] Filed: May 9, 1997

[51] Int. Cl.⁶ .................................................. A61B 17/39
[52] U.S. Cl. ............................................. 606/47; 606/45
[58] Field of Search ................................ 606/41, 45–47, 606/28

[56] References Cited

U.S. PATENT DOCUMENTS

| | | |
|---|---|---|
| 2,843,128 | 7/1958 | Storz . |
| 4,325,374 | 4/1982 | Komiya . |
| 4,811,735 | 3/1989 | Nash et al. . |
| 4,846,174 | 7/1989 | Willard et al. . |
| 5,024,617 | 6/1991 | Karpiel . |
| 5,026,371 | 6/1991 | Rydell et al. . |
| 5,053,044 | 10/1991 | Mueller et al. . |
| 5,071,424 | 12/1991 | Reger . |
| 5,075,062 | 12/1991 | Karpiel ..................................... 264/173 |
| 5,092,872 | 3/1992 | Segalowitz . |
| 5,152,772 | 10/1992 | Sewell, Jr. . |
| 5,163,942 | 11/1992 | Rydell . |
| 5,201,732 | 4/1993 | Parins et al. ............................... 606/47 |
| 5,241,970 | 9/1993 | Johlin, Jr. et al. . |
| 5,423,844 | 6/1995 | Miller . |
| 5,609,601 | 3/1997 | Kolesa et al. ............................. 606/170 |
| 5,620,440 | 4/1997 | Heckele et al. ............................ 606/28 |
| 5,685,201 | 11/1997 | Braun ....................................... 81/63.1 |
| 5,769,848 | 6/1998 | Wattanasirichaigoon ................. 606/46 |

*Primary Examiner*—Lee Cohen
*Assistant Examiner*—Roy Gibson
*Attorney, Agent, or Firm*—Thomas I. Rozsa; Tony D. Chen; Jerry Fong

[57] ABSTRACT

A rotatable sphincterotome/papillotome is inserted into a flexible endoscope and is used for orienting the distal cutting wire tip of the rotatable sphincterotome/papillotome in a twelve o'clock position, where the distal cutting wire tip cuts the sphincter muscle of a patient. The sphincterotome has a housing and a flexible tubular member protruding from the housing. A slidable member is slidably connected on the housing for moving the distal cutting wire tip in a longitudinal direction to cut the sphincter muscle. A ratchet mechanism is rotatably attached to the housing for orienting the angle of the distal cutting wire tip to a correct cutting position, where the gripping assembly is rotatable on the ratchet mechanism. To change the angle of the distal cutting wire tip of the sphincterotome, a user must use one hand to hold the ratchet mechanism while the other hand rotates the housing, and thereby the angle of the distal cutting wire tip changes to a specific degree. The ratchet mechanism is able to change the angle of the cutting wire by rotating it to the desired degree so that the angle of the cutting wire will be at the correct cutting position when the cutting takes place.

41 Claims, 3 Drawing Sheets

ROTATABLE SPHINCTEROTOME/PAPILLOTOME AND METHOD OF USE

BACKGROUND OF THE INVENTION

1. Field of the Invention

The present invention relates generally to the field of sphincterotomy. More particularly, the present invention relates to the field of medical devices such as sphincterotomes/papillotomes to provide controlled bending and orienting during cutting of the patient's sphincter.

2. Description of the Prior Art

In endoscopic sphincterotomy, sphincterotomes and more specifically papillotomes, are used in conjunction with an endoscope to provide surgical cutting inside of a patient. The sphincterotome/papillotome may be used to partially cut open the sphincter muscle for treatment such as removal of common bile duct stones forming an obstruction. The prior art sphincterotomes/papillotomes include the blade cutting wire for cutting the sphincter muscle. The disadvantage with prior art sphincterotome/papillotome is that when it is fished through the body and the cutting wire comes in contact with the sphincter muscle, the precise angle at which the cutting wire is located relative to the sphincter muscle cannot be accurately controlled and it is a hit or miss procedure. The angle of the cutting wire must be exactly twelve o'clock position in order to properly cut the sphincter muscle.

The following eleven (11) prior art patents are found to be pertinent to the field of the present invention:

1. U.S. Pat. No. 2,843,128 issued to Storz on Jul. 15, 1958 for "Adenotome" (hereafter the "Storz Patent");
2. U.S. Pat. No. 4,811,735 issued to Nash et al. on Mar. 14, 1989 for "Stone Destroying Catheter And Method Of Use" (hereafter the "Nash Patent");
3. U.S. Pat. No. 5,024,617 issued to Karpiel on Jun. 18, 1991 for "Sphincterotomy Method And Device Having Controlled Bending And Orientation" (hereafter the "Karpiel Patent");
4. U.S. Pat. No. 5,026,371 issued to Rydell et al. on Jun. 25, 1991 for "Handle For Polypectome Snare With Bipolar Electrodes " (hereafter the "'371 Rydell Patent");
5. U.S. Pat. No. 5,053,044 issued to Mueller et al. on Oct. 1, 1991 for "Catheter And Method For Making Intravascular Incisions" (hereafter the "Mueller Patent");
6. U.S. Pat. No. 5,071,424 issued to Reger on Dec. 10, 1991 for "Catheter Atherotome" (hereafter the "Reger Patent");
7. U.S. Pat. No. 5,092,872 issued to Segalowitz on Mar. 3, 1992 for "Valvulotome Catheter" (hereafter the "Segalowitz Patent");
8. U.S. Pat. No. 5,152,772 issued to Sewell, Jr. on Oct. 6, 1992 for "Sphincterotomy Catheter And Method" (hereafter the "Sewell Patent");
9. U.S. Pat. No. 5,163,942 issued to Rydell on Nov. 17, 1992 for "Surgical Instrument With Grasping Loop For Laparoscopic Procedures" (hereafter the "'942 Rydell Patent");
10. U.S. Pat. No. 5,241,970 issued to Johlin, Jr. et al. on Sep. 7, 1993 for "Papillotome/Sphincterotome Procedures And A Wire Guide Specially Suited Therefor" (hereafter the "Johlin Patent"); and
11. U.S. Pat. No. 5,423,844 issued to Miller on Jun. 13, 1995 for "Rotary Surgical Cutting Instrument" (hereafter the "Miller Patent").

The Storz Patent discloses an adenotome. It comprises a body with a bar slidable in the body. A pair of finger-receiving rings are fixed to the left hand end of the body and a thumb receiving ring swivels on the corresponding end of the bar.

The Nash Patent discloses a stone destroying catheter and method of use. It comprises a small diameter catheter with a longitudinal axis and a working head located at the distal end. The catheter is capable of being located at any position within the body so that the working head is adjacent the stone. The working head is rotated at high speed about the longitudinal axis of the catheter.

The Karpiel Patent discloses a sphincterotomy method and device having controlled bending and orientation. It comprises a multi-lumen tubular member, with one lumen having an electrical conductor, and the other lumen having a reinforcing wire. The reinforcing wire has a rectangular cross-section, providing a greater moment of inertia in a resisting axis than in a bending axis.

The '371 Rydell Patent discloses a handle for polypectome snare with bipolar electrodes.

The Mueller Patent discloses a catheter and method for making intravascular incisions. The vascular catheter includes a blade tip at its distal end. The blade is mounted within the blade tip and a mechanism is provided for extending the blade transversely when the blade tip is located within a region of stenosis.

The Reger Patent discloses a catheter atherotome.

The Segalowitz Patent discloses a valvulotome catheter. It is used for cutting the bi-cuspid venous valves free from the wall of a vein to be used in bypass vein graft surgery. The end portion is rotatably supported from a tube by way of a shaft. The shaft terminates at its distal end in a blade support member which carries the longitudinally fixed cutting blades. Rotation of the shaft enhances the cutting of the catheter.

The Sewell Patent discloses a sphincterotomy catheter and method. It comprises an elongated longitudinal channel, two separate balloons located at the distal end of the catheter, and a cutting means extendable from the catheter between the balloons. The first balloon is inflated by introducing a gas or a fluid to a first port which flows through the first lumen into the first balloon. Similarly, the second balloon is inflated by introducing a gas or a fluid to a second port which flows through the second lumen and into the second balloon.

The '942 Rydell Patent discloses a surgical instrument with a grasping loop for laparoscopic procedures. It comprises a knob which is rotatable and causes a pinion gear to be turned clockwise, engaging both racks. The rack will be moved toward a proximal end as the rack moves toward a distal end of the handle, thus effectively rotating the grasping loop and any tissue held therein.

The Johlin Patent discloses papillotome/sphincterotome procedures and a wire guide specially suited therefor. The wire guide comprises an outer insulative tube, an inner shaft and a platinum coil at its distal end. The outer tube loosely accommodates the inner shaft with a cushion of air therebetween for additional insulative effect, and the platinum alloy coil is also loosely positioned within the outer tubing.

The Miller Patent discloses a rotary surgical cutting instrument which is used for cutting tissue within an anatomical space. It comprises an outer cannula for percutaneous insertion into the anatomical space. The outer cannula has a central bore along its length and a cutting opening adjacent the distal end sized to receive tissue therethrough. A rotatably driven tubular cutting member is disposed within the central bore of the outer cannula, with a cutting edge rotating beneath the cutting opening of the cannula It is highly desirable to have a very efficient and also very effective design and construction of a rotatable sphincterotome/papillotome device to enhance the control which a physician has in performing a sphincterotomy, and provides a reduced risk of inadvertent or uncontrolled cuts which may injure the patient. It is also desirable to provide an improved device with the capability of orienting the angle of the cutting wire to the exact cutting position (between 11 o'clock to 1 o'clock) when the device exits the endoscope for cutting the sphincter muscle. It is further desirable to provide an improved device which overcomes the limitations of other devices and provides for a controlled, and safer cutting of the sphincter muscle. Furthermore, the device does not have to exit the endoscope in the correct orientation, because through visualizing the angle with the endoscope and through the ratchet rotating mechanism, the angle of the cutting wire can be rotated to the exact cutting position at all times before the sphincter muscle is cut. Accordingly, the physician maintains a greater control during endoscopic sphincterotomy, and reduces the risk of improper cuts and the associated complications.

SUMMARY OF THE INVENTION

The present invention is a novel and unique rotatable sphincterotome/papillotome device (hereafter referred as the "sphincterotome device") and method of use. The sphincterotome device is inserted into a flexible endoscope and for orienting the distal cutting wire tip of the rotatable sphincterotome device between a range of approximately eleven (11) o'clock to one (1) o'clock, where the distal cutting wire tip cuts the sphincter muscle of a patient. The rotatable sphincterotome device comprises a housing and a flexible tubular member protruding from the proximal end of the housing. A gripping assembly is slidably connected on a housing for moving the distal cutting wire tip in a longitudinal direction to cut the sphincter muscle and a ratchet mechanism for orienting the angle of the distal cutting wire tip approximately between eleven o'clock position to one o'clock position, where the gripping assembly is rotatable on the ratchet mechanism.

To change the angle of the distal cutting wire tip of the sphincterotome device, a user must use one hand to hold the ratchet mechanism while the other hand rotates the gripping assembly, and thereby the angle of the distal cutting wire tip changes to a specific degree.

Specifically, this device is used to cut the sphincter muscle which leads to the gallbladder so that stones which form in the gallbladder and move out of the gallbladder and are blocked by the sphincter muscle can be subsequently removed after the sphincter muscle is cut.

The overall device includes the blade cutting wire for cutting the sphincter muscle which is already known in the prior art. What is unique about the present invention is that it has a ratchet mechanism so that the angle of the cutting wire can be rotated to the desired degree so that the angle of the cutting wire will be approximately between an eleven o'clock position to an one o'clock position when the cutting takes place between the preferred angle. Typically, as the device is fished through the body and the cutting wire comes in contact with the sphincter muscle, the precise angle at which the wire is located relative to the sphincter muscle cannot be accurately controlled. With the present invention, through visualizing the angle with the endoscope and through the ratchet mechanism, the angle of the cutting wire can be rotated to the correct cutting position before the sphincter muscle is cut.

It is an object of the present invention to provide a sphincterotome device having a cutter which can be oriented every time to a correct cutting position, for example, approximately between 11–1 o'clock position for cutting a patient's sphincter muscle.

It is a further object of the present invention to provide a sphincterotome device having controlled bending of the distal end cutting wire for cutting a patient's sphincter muscle.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DESCRIPTION OF THE PREFERRED EMBODIMENT

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
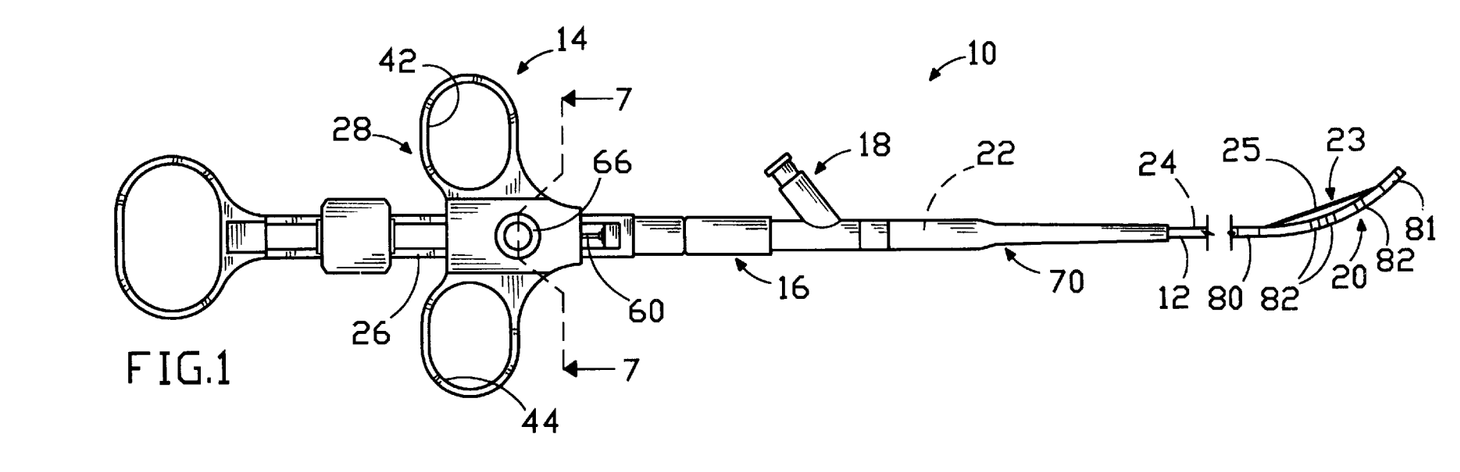
FIG. 1 is a side elevational view of the present invention rotatable sphincterotome/papillotome device.
Figure 2:
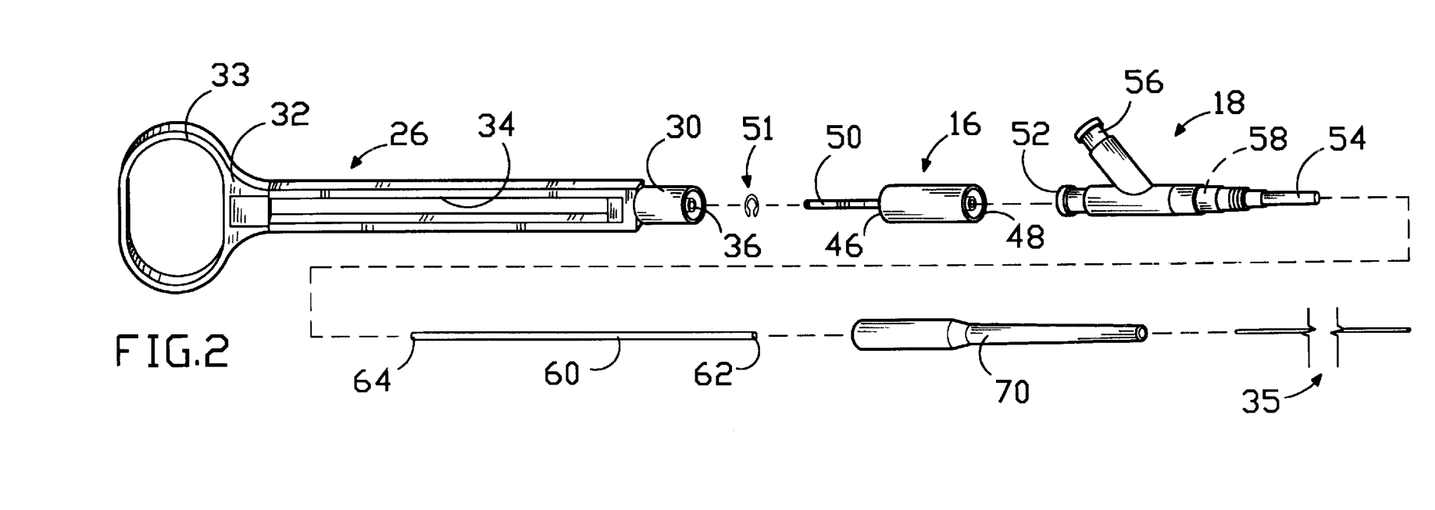
FIG. 2 is a partial exploded perspective view showing the rigid rotatable housing, a ratchet mechanism, a two-way fitting member, a circular rod and a heat shrink tubing.

Referring to FIG. 1, there is illustrated at 10 a preferred embodiment of the present invention sphincterotome/papillotome device (hereafter referred as the "sphincterotome device") and method of use, and constructed in accordance with the present invention. Referring to FIGS. 1 and 2, the sphincterotome device 10 comprises an elongated tubular member 12, a control hand gripping assembly 14, a ratchet mechanism 16, and a two-way fitting member 18. The tubular member 12 is preferably translucent and has a distal end 20, a proximal end 22, and a lumen 24 which extends the full length of the tubular member 12, and sized to be received in a flexible endoscope lumen (not shown) and passes within the lumen of the endoscope. The tubular member 12 is preferably extruded from a flexible plastic material, such as Teflon®, polyethylene or other medical grade plastic material.

Figure 4:
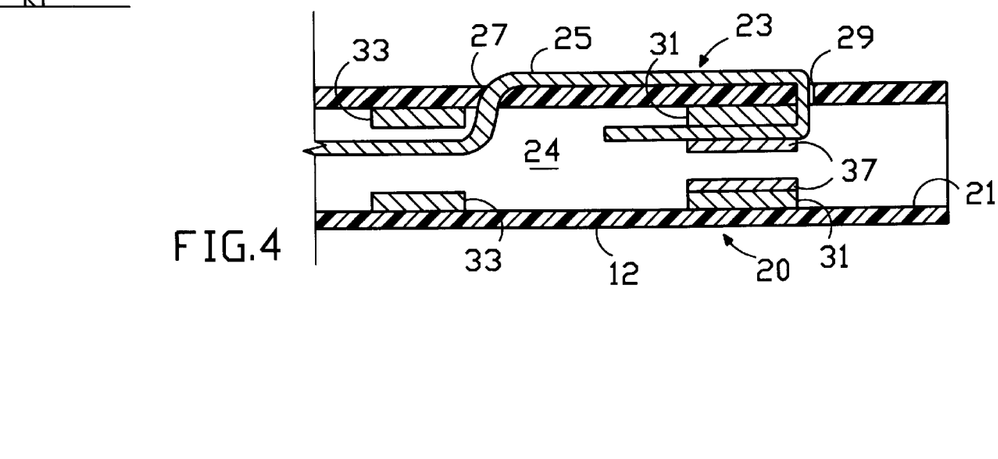
FIG. 4 is an enlarged partial longitudinal cross-sectional view of the distal end cutting wire of the present invention rotatable sphincterotome device.

Referring to FIG. 4, there is illustrated a partial cross-sectional view of the distal end 20 of the tubular member 12. A cutter means 23 is provided on the outside of the tubular member 12 and includes a cutting edge 25 located along the distal end 20 of tubular member 12 and between a first location 27 and a second location 29. The cutter means 23 is bowed between the first location 27 and a second location 29 on the outside of the tubular member 12, wherein the first location 27 has a small aperture therein and the second location 29 has a slotted aperture therein (see FIG. 5). The tubular member 12 is provided with two distal cylindrical tubes 31 and 37, and an opposing proximal cylindrical tube 33. The distal and proximal cylindrical tubes 31 and 33 are affixed to the interior wall of the lumen 24 of tubular member 12 by adhesive or any other suitable means and located adjacent to the second and first location apertures 29 and 27 respectively. The distal cylindrical tube 37 is affixed to the interior of the distal cylindrical tube 31 by adhesive or any other suitable means. By way of example only, to install the cutter means 23, it may be accomplished by having the cutter means 23 exit the wall of tubular member 12 at the first location aperture 27 and reenter the wall of tubular member 12 at the second location aperture 29 and secured between the two distal cylindrical tubes 31 and 37. Of course the installation of the cutter means is not intended to be restricted to this particular arrangement, since this is but one of many ways to install the cutter means, and it is within the spirit and scope of the present invention to utilize other ways to install the cutter means.

The other end of the cutter means 23 is located within the proximal cylindrical tube 33. These cylindrical tubes 31, 33 and 37 stabilize and support the cutter means 23 within the tubular member 12 for any movement. The cutter means 23 is positioned generally longitudinally with respect to the tubular member 12, wherein the cutting edge 25 is movable in a cutting plane to cut a patient's sphincter or etc.

Figure 3:
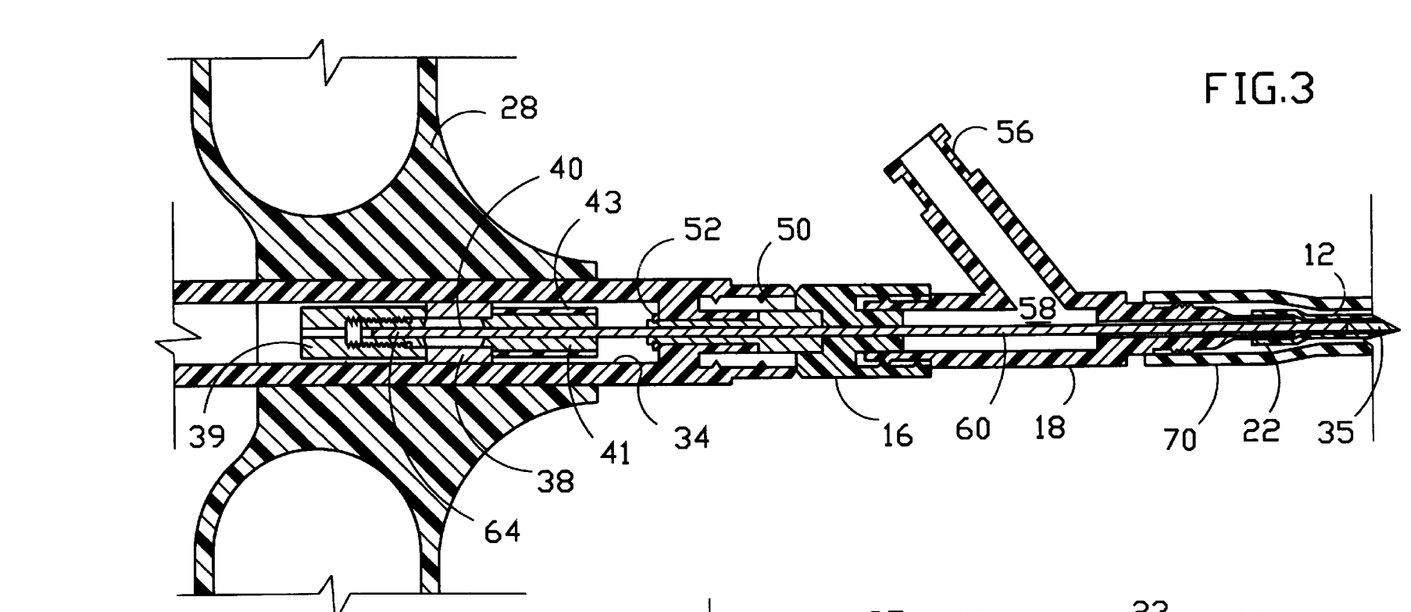
FIG. 3 is an enlarged partial longitudinal cross-sectional view of the present invention rotatable sphincterotome device.

Referring to FIGS. 2, 3 and 4, there is illustrated a partial electrical conductor wire 35 which is disposed in the lumen 24 of tubular member 12 and extends almost the full length of the tubular member 12 and connected to the cutter means 23 by any suitable means, thereby making up an electrically conductive cutter means 23 at the distal end 20 of the tubular member 12.

Referring to FIGS. 1, 2 and 3, the control gripping assembly 14 includes a rotatable rigid housing 26 of a predetermined length and a slidable finger member 28. The rotatable housing 26 has a proximal end 30, a distal end 32, and a longitudinal slot 34 formed between the proximal end 30 and the distal end 32. The proximal end 30 is provided with a channel opening 36 therein, which communicates with the longitudinal slot 34. The rotatable housing 26 further has a thumb receiving member 33 affixed at the distal end 32 for receiving the user's thumb and extending laterally on opposed sides of the housing 26 are a pair of lateral finger gripping members 42 and 44 which are shown as being oval in shape for receiving the forefinger and index finger of the user's hand. The hand gripping assembly 12 is preferably formed by molding its pieces from a rigid plastic material or any other way known in the art. The slidable finger member 28 has a slide block 38 (see FIGS. 3 and 7) fitted into the longitudinal slot 34. The two opposite interior walls of the longitudinal slot 34 constrain the slide block 38 to longitudinal movement between the proximal end 30 and the distal end 32 of the housing 26. A longitudinally extending channel 40 (see FIG. 3) is formed in the slide block 38.

The ratchet mechanism 16 has a proximal end 46, a distal connecting end 48, and a hollow pivotable post 50 permanently affixed to the proximal end 46 by adhesive or any other suitable means. The ratchet mechanism 16 is installed by inserting the hollow pivotable post 50 into the channel opening 36 at the proximal end 30 of the housing 26 and partially extends into the longitudinal slot 36, where a lock washer 51 secures the hollow pivotable post 50 thereto and prevents the ratchet mechanism from longitudinal movements. Once the ratchet mechanism 16 is secured, the proximal end 46 abuts against the proximal end 30 of the housing 26 so that the housing 26 can be rotated on the pivotable post 50.

The two-way fitting member 18 has a proximal connecting end 52 connected to the distal connecting end 48 of ratchet mechanism 16, a distal end 54, a side connecting port 56, and a lumen 58 extending from the distal end 54 to the proximal connecting end 52 and the side connecting port 56. The distal end 54 is attached to the proximal end 22 of the tubular member 12. The side connecting port 56 may be coupled to a supply fluid, such as fluoroscopic contrast media, to supply the contrast media out through an opening 21 located at the distal end 20 of the tubular member 12. In addition, the side connecting port 56 may be used for inserting a guide wire (not shown) therethrough and into the tubular member 12 for guiding the distal end 20 of the tubular member 12 in the patient. The side connecting port 56 may accept guide wires that are approximately 0.021" or 0.035"; 0.035" guide wires being the most commonly used in the industry.

Referring to FIGS. 2 and 3, there is shown a lengthy circular rod 60 which is provided with the present invention sphincterotome device 10 and preferably made of stainless steel or any other suitable material. The circular rod 60 is movably disposed in the lumen 58 of fitting member 18 and partially extends out from the distal connecting end 54 of fitting member 18 and also from the hollow pivotable post 50 of ratchet mechanism 16. The circular rod 60 has one end 62 affixed to the conductor wire 35 and the other end 64 inserted into the slide block 38 and tightly secured thereto by a knob 66 which is provided on the slidable finger member 28, where the knob 66 can be tightened on the other end 64 of the circular rod 60.

Figures 5, 6, 7, 8:
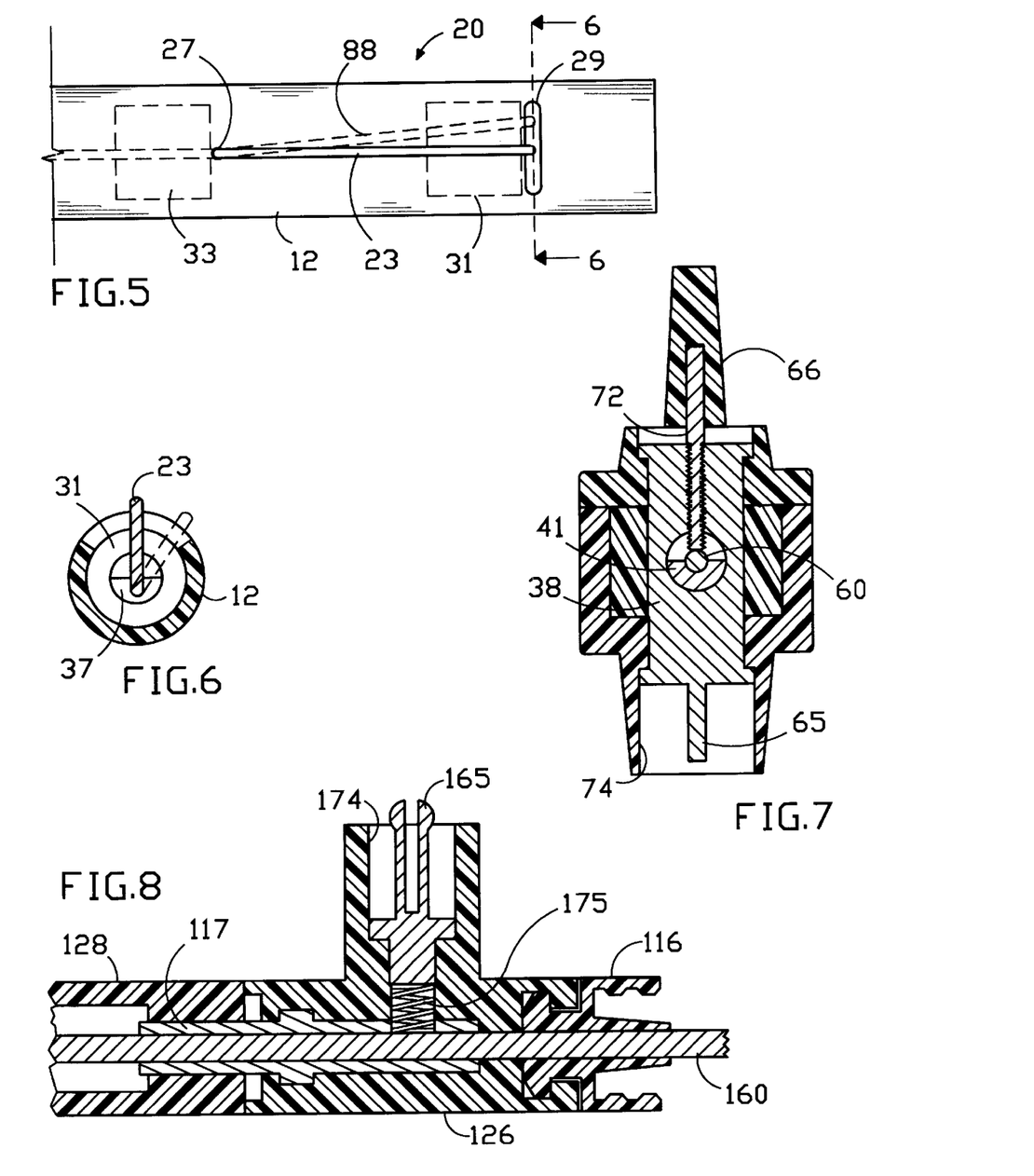
FIG. 5 is an enlarged partial top plan view of the distal end cutting wire of the present invention rotatable sphincterotome device shown in FIG. 4.
FIG. 6 is a cross-sectional view taken along line 6—6 of FIG. 5.
FIG. 7 is an enlarged cross-sectional view taken along line 7—7 of FIG. 1.
FIG. 8 is a partial enlarged cross-sectional view of an alternative embodiment of the present invention rotatable sphincterotome device, showing an electrical wire connection.

Referring to FIG. 7, there is shown enlarged cross-sectional view of knob 66 and its associated parts. The knob 66 may be turned either in the clockwise or counter-clockwise direction to tighten or loosen its threaded shaft 72 onto the end 64 of circular rod 60 to secure the circular rod 60 in place. On the opposite side of the slidable finger member 28 is a recess 74, where an electrical wire connection 65 is provided for high frequency electrical current to the cutter means 23 which is well known in the art and will not be described.

Referring to FIGS. 3 and 6, the slide block 38 includes a cap means 39 threaded onto a supporting rod means 41 for supporting the circular rod 60. A rubber cap means 43 is partially covering the supporting rod means 41. The longitudinal channel 40 receives the circular rod 60 therein and is secured thereto by the threaded shaft 72 of knob 66 (see FIG. 7).

Referring to FIG. 3, the sphincterotome device 10 further comprises a heat shrink tubing 70 which encloses the proximal end 22 of the tubular member 12 and the distal end 54 of the fitting member 18 for providing strain relief.

Referring to FIG. 1, the sphincterotome device 12 may further comprise indicating means 80, 81 and 82 at the distal end 20 of tubular member 12 for providing visual indication of the position of the distal end 20 in the patient.

The operation of the foregoing embodiment now will be described. Referring to FIGS. 1 through 7, the slidable finger member 28 is drawn distally towards the distal end 32 of the rotatable housing 26 to exert traction on the circular rod 60 which in turn pulls the conductor wire 35 to cause the cutter means 23 to pull tight as is known. Upon energizing the conductor wire 35 which in turn energizes the cutter means 23, which in turn energizes the cutting edge 25 in the cutting plane to cut the muscle radially outward of a center of the patient's sphincter, the slidable finger member 28 is drawn distally to move the cutter edge 25 in a cutting plane to cut a patient's sphincter. Such movement is caused by tensioning the circular rod 60 which in turn causes the conductor wire 35 to pull on the cutter means 23 through the first location aperture 27, causing the second location 29 to be drawn proximally and causing the cutting edge 25 to sweep through cutting plane. It will be appreciated, however, that when the slidable finger member 28 is pushed forward, i.e., in the proximal end 30 of rotatable housing 26, the cutter means 23 will return to its initial position, parallel to the tubular member 12.

Referring to FIGS. 3, 5 and 6, another feature of the sphincterotome device 10 is that the cutter means 23 can be rotated to the left side or right side of the tubular member 12. To position the cutter means 23 in a correct cutting position, such as approximately between eleven (11) o'clock to one (1) o'clock, a user must hold the ratchet mechanism 16 in one hand while using the other hand to rotate the rotatable housing 26 in either direction to cause the cutting edge 25 of cutter means 23 to move to the left side or the right side of the tubular member 12, so that it will be in a correct cutting position to cut the patient's sphincter. By way of example, after one or two rotations of the rotatable housing 26, the cutter means 23 is located at a different location 88 which is shown in dashed lines in FIG. 5. This is accomplished because the circular rod 60 is securely held by the knob 66 to the slide block 38 and the hollow pivotable post 50 is rotated within the channel opening 36 of housing 26, thereby causing the circular rod 60 to rotate in either direction which in turn causes the conductor wire 35 to rotate, which in turn causes the cutter means 23 to move in the left side or the right side of the tubular member 12 (FIG. 6 shows dashed lines of the cutter means 23 moved to the right side of the tubular member 12).

It will be appreciated that the rotatable sphincterotome device 10 conforms to conventional forms of manufacture or any other conventional way known to one skilled in the art.

Referring to FIG. 8, there is illustrated an alternative embodiment of another means of a rotatable housing 126 of the present invention sphincterotome device. Since it assembles and functions the same as previously described above except that a handle means 128, a rotatable housing 126, and the ratchet mechanism 116 are substituted for the slidable finger member 28, the rigid housing 26, and the ratchet mechanism 16 respectively, the parts are numbered correspondingly with 100 added to each number. A hollow steel tubing 117 is fixed within the handle means 128, the rotatable housing 126 and the ratchet mechanism 116. A circular rod 160 which is identical to the circular rod 60 in FIGS. 1 through 7 is installed within the hollow steel tubing 117 such that the ends of the circular rod 160 extend out from the handle means 128 and the ratchet mechanism 116. The circular rod 160 is connected to an electrical conductor wire (not shown) but is similar to way it is connected in FIGS. 1 through 7, and the description will not be repeated. The rotatable housing 126 has a side recess 174, where an electrical wire connection 165 is provided for high frequency electrical current to the cutter means. A biasing spring 175 is installed within the side recess 174 and biasing the circular rod 160 for keeping the circular rod 160 in relationship with the handle means 128 and the rotatable housing 126. To position the cutter means (shown in FIGS. 1, 4 and 5) in a correct cutting position, such as approximately between eleven (11) o'clock to one (1) o'clock position, a user must hold the ratchet mechanism 116 in one hand while using the other hand to rotate the rotatable housing 126 in either direction (left or right) to cause the cutting edge of cutter means to move to the left side or the right side of the tubular member, so that it will be in a correct cutting position to cut the patient's sphincter or etc. This is accomplished because the circular rod 160 is securely held within the steel tubing 117 by the biasing spring 175, whereby holding the rachet mechanism 116 and rotating the rotatable housing 126 causes the circular rod 160 to rotate with the rotatable housing 126 but within the ratchet mechanism 116 which in turn causes the conductor wire to rotate, which in turn causes the cutter means to move in the left side or right side of the tubular member.

Defined in detail, the present invention is a sphincterotome device used in conjunction with an endoscope for cutting a patient's sphincter, the device comprising: (a) an elongated tubular member having a proximal end and a distal end, and being sized to be received in the lumen of the endoscope; (b) a cutter member having a cutting edge located along the distal end of the tubular member and positioned generally longitudinally with respect to the tubular member, wherein the cutting edge is movable in a cutting plane to cut the patient's sphincter, the cutter member being connected to a conductor disposed in the tubular member; (c) a fitting member having a distal end, a proximal end, and at least one lumen therein extending from the distal end to the proximal end, the distal end attached to the proximal end of the tubular member; (d) a rigid rotatable housing of a predetermined length having a proximal end, a distal end and a longitudinal slot formed between the proximal and distal ends, the proximal end having a channel opening therein and extending into the longitudinal slot, the rotatable housing further having a thumb receiving member affixed to the distal end; (e) a ratchet mechanism attached between the rotatable housing and the fitting member, and having a distal connecting end connected to the proximal end of the fitting member, a proximal end rotationally abutting against the proximal end of the rotatable housing, and a hollow pivotable post permanently affixed to the proximal end of the ratchet mechanism, the hollow pivotable post inserted into the channel opening at the proximal end of the rotatable housing so that the hollow pivotable post is rotatably secured within the channel opening at the proximal end of the rotatable housing; (f) a circular rod movably disposed in the at least one lumen of the fitting member and having a distal end extending out from the distal end of the fitting member and connected to the conductor, and a proximal end exiting out from the hollow pivotable post; (g) a slidable member including a slide block fitted into the longitudinal slot and a pair of extending finger receiving members extending oppositely and transversely from the slide block, the walls of the longitudinal slot constraining the slide block to longitudinal movement between the proximal and distal ends of the rotatable housing with one longitudinally extending channel formed in the slide block for receiving and securing the proximal end of the circular rod therein, where holding the ratchet mechanism and rotating the rotatable housing can orient the cutting edge of the cutter member into a correct cutting position for cutting the patient's sphincter; and (h) at least one cylindrical tube affixed within the tubular member and located adjacent to the distal end for stabilizing and supporting the cutter member.

Defined broadly, the present invention is a sphincterotome device used in conjunction with an endoscope for cutting a patient's sphincter, the device comprising: (a) a tubular member having a proximal end and a distal end, the distal end extending into the endoscope and into engagement with the patient's sphincter; (b) a cutter member having a cutting edge located along the distal end of the tubular member and positioned generally longitudinally with respect to the tubular member, wherein the cutting edge is movable in a cutting plane to cut the patient's sphincter, the cutter member being connected to a conductor disposed in the tubular member; (c) a fitting member having a distal end, a proximal end, and at least one lumen therein extending from the distal end to the proximal end, the distal end attached to the proximal end of the tubular member; (d) a rotatable housing having a proximal end, a distal end and a longitudinal slot formed between the proximal and distal ends, the proximal end having a channel opening therein and extending into the longitudinal slot; (e) a ratchet mechanism attached between the rotatable housing and the fitting member, and having a distal connecting end connected to the proximal end of the fitting member, a proximal end rotationally abutting against the proximal end of the rotatable housing, and a pivotable post affixed to the proximal end of the ratchet mechanism, the pivotable post inserted into the channel opening at the proximal end of the rotatable housing so that the pivotable post is rotatably secured within the channel opening at the proximal end of the rotatable housing; (f) a rod movably disposed in the at least one lumen of the fitting member and having a distal end extending out from the distal end of the fitting member and connected to the conductor, and a proximal end exiting out from the pivotable post; and (g) a slidable member including a slide block fitted into the longitudinal slot so that the walls of the longitudinal slot constrain the slide block to longitudinal movement between the proximal and distal ends of the rotatable housing with one longitudinally extending channel formed in the slide block for receiving and securing the proximal end of the rod therein, where holding the ratchet mechanism and rotating the rotatable housing can orient the cutting edge of the cutter member into a correct cutting position for cutting the patient's sphincter.

Defined more broadly, the present invention is a sphincterotome used in conjunction with an endoscope for cutting a patient's sphincter or like, comprising: (a) a tubular member having a proximal end and a distal end, the distal end extending into the endoscope and into engagement with the patient's sphincter; (b) a cutter member having a cutting edge located along the distal end of the tubular member, wherein the cutting edge is movable in a cutting plane to cut the patient's sphincter, the cutter member being connected to a conductor disposed in the tubular member; (c) a rotatable housing having a slot formed therein; (d) a ratchet mechanism attached between the rotatable housing and the proximal end of the tubular member, and having a pivotable post rotatably secured within the slot of the rotatable housing; (e) a rod movably disposed in the ratchet mechanism and having one end connected to the conductor; and (f) a slidable member movably connected in the slot and having means for receiving and securing the other end of the rod therein, where holding the ratchet mechanism and rotating the rotatable housing can orient the cutting edge of the cutter member into a correct cutting position for cutting the patient's sphincter.

Defined even more broadly, the present invention is a papillotome, comprising: (a) a tubular member having a proximal end and a distal end; (b) a cutter member having a cutting edge located along the distal end of the tubular member, wherein the cutting edge is movable in a cutting plane to cut a patient's muscle, the cutter member being connected to a conductor disposed in the tubular member; (c) a ratchet mechanism attached to the proximal end of the tubular member; (d) a rod disposed in the ratchet mechanism and having one end connected to the conductor; and (e) means for rotatably retaining the ratchet mechanism, and means for receiving and securing the other end of the rod, where holding the ratchet mechanism and turning the rotatably retaining means can orient the cutter member in a correct angle for cutting the patient's muscle.

Alternatively defined in detail, the present invention is a method of surgically cutting a patient's sphincter, the method comprising the steps of: (a) positioning an endoscope near the patient's sphincter to allow viewing of the sphincter; (b) providing a sphincterotome device having a tubular member with a proximal end and a distal end; (c) inserting the distal end of the tubular member out of an opening of the endoscope and into engagement with the patient's sphincter; (d) longitudinally positioning a cutter member which has a cutting edge located along the distal end of the tubular member, wherein the cutting edge is movable in a cutting plane to cut the patient's sphincter, and connecting the cutter member to a conductor disposed in the tubular member; (e) providing a rotatable housing means having a longitudinal slot formed therein; (f) attaching a ratchet mechanism between the rotatable housing means and the proximal end of the tubular member, and rotatably securing a pivotable post to the rotatable housing means; (g) disposing a rod in the ratchet mechanism and connecting one end of the rod to the conductor; (h) sidably connecting a slidable member in the longitudinal slot to move in a longitudinal movement and providing means for receiving and securing the other end of the rod therein; (i) holding the ratchet mechanism and rotating the rotatable housing means which orients the cutting edge of the cutter member into a correct cutting position for cutting the patient's sphincter; and (j) energizing the conductor with the cutter member with the cutting edge in the cutting plane to cut the sphincter radially outward of a center of the sphincter.

Alternatively defined broadly, the present invention is a method of surgically cutting a patient's muscle, the method comprising the steps of: (a) positioning an endoscope near the patient's muscle to allow viewing of the muscle; (b) providing a papillotome having a tubular member; (c) inserting the tubular member out of an opening of the endoscope and into engagement with the muscle; (d) positioning a cutter member which has a cutting edge along a respective end of the tubular member, wherein the cutting edge is movable in a cutting plane to cut the patient's muscle; (e) attaching a ratchet mechanism to the respective end of the tubular member; (f) disposing a rod in the ratchet mechanism and connecting one end thereof to the cutter member; (g) holding the ratchet mechanism and rotating the rod which orients the cutting edge of the cutter member into a correct cutting position for cutting the patient's muscle; and (h) energizing the cutter member with the cutting edge in the cutting plane to cut the muscle radially outward of a center of the muscle.

Alternatively defined more broadly, the present invention is a method of surgically cutting a patient's muscle, the method comprising the steps of: (a) positioning a cutter member adjacent to the patient's muscle; and (b) orienting the cutting member by rotating a rod connected to the cutting member so that the cutting member can move in a correct cutting plane to cut the patient's muscle.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modifications in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. A sphincterotome device used in conjunction with an endoscope for cutting a patient's sphincter, the device comprising:

a. an elongated tubular member having a proximal end and a distal end, and being sized to be received in a lumen of the endoscope;

b. a cutter member having a cutting edge located along said distal end of said tubular member and positioned generally longitudinally with respect to said tubular member, wherein the cutting edge is movable in a cutting plane to cut the patient's sphincter, the cutter member being connected to a conductor disposed in said tubular member;

c. a fitting member having a distal end, a proximal end, and at least one lumen therein extending from the distal end to the proximal end, the distal end attached to said proximal end of said tubular member;

d. a rigid rotatable housing of a predetermined length having a proximal end, a distal end and a longitudinal slot formed between the proximal and distal ends, the proximal end having a channel opening therein and extending into the longitudinal slot, the rotatable housing further having a thumb receiving member affixed to the distal end;

e. a ratchet mechanism attached between said rotatable housing and said fitting member, and having a distal connecting end connected to said proximal end of said fitting member, a proximal end rotationally abutting against said proximal end of said rotatable housing, and a hollow pivotable post permanently affixed to the proximal end of the ratchet mechanism, the hollow pivotable post inserted into said channel opening at said proximal end of said rotatable housing so that the hollow pivotable post is rotatably secured within said channel opening at said proximal end of said rotatable housing;

f. a circular rod movably disposed in said at least one lumen of said fitting member and having a distal end extending out from said distal end of said fitting member and connected to said conductor, and a proximal end exiting out from said hollow pivotable post;

g. a slidable member including a slide block fitted into said longitudinal slot and a pair of extending finger receiving members extending oppositely and transversely from the slide block, the walls of said longitudinal slot constraining the slide block to longitudinal movement between said proximal and distal ends of said rotatable housing with one longitudinally extending channel formed in the slide block for receiving and securing said proximal end of said circular rod therein, where holding said ratchet mechanism and rotating said rotatable housing can orient said cutting edge of said cutter member into a correct cutting position for cutting the patient's sphincter; and h. at least one cylindrical tube affixed within said tubular member and located adjacent to said distal end for stabilizing and supporting said cutter member.

2. The sphincterotome device in accordance with claim 1 further comprising a heat shrink tubing for enclosing said proximal end of said tubular member and said distal end of said fitting member for providing strain relief.

3. The sphincterotome device in accordance with claim 1 further comprising indicating means at said distal end of said tubular member for providing visual indication of the position of said distal end of said tubular member in the patient.

4. The sphincterotome device in accordance with claim 1 wherein said cutter member comprises a wire bowed between first and second locations at said distal end of said tubular member.

5. The sphincterotome device in accordance with claim 1 wherein said tubular member has an opening at said distal end.

6. A sphincterotome device used in conjunction with an endoscope for cutting a patient's sphincter, the device comprising:

a. a tubular member having a proximal end and a distal end, the distal end extending into said endoscope and into engagement with the patient's sphincter;

b. a cutter member having a cutting edge located along said distal end of said tubular member and positioned generally longitudinally with respect to said tubular member, wherein the cutting edge is movable in a cutting plane to cut the patient's sphincter, the cutter member being connected to a conductor disposed in said tubular member;

c. a fitting member having a distal end, a proximal end, and at least one lumen therein extending from the distal end to the proximal end, the distal end attached to said proximal end of said tubular member;

d. a rotatable housing having a proximal end, a distal end and a longitudinal slot formed between the proximal and distal ends, the proximal end having a channel opening therein and extending into the longitudinal slot;

e. a ratchet mechanism attached between said rotatable housing and said fitting member, and having a distal connecting end connected to said proximal end of said fitting member, a proximal end rotationally abutting against said proximal end of said rotatable housing, and a pivotable post affixed to the proximal end of the ratchet mechanism, the pivotable post inserted into said channel opening at said proximal end of said rotatable housing so that the pivotable post is rotatably secured within said channel opening at said proximal end of said rotatable housing;

f. a rod movably disposed in said at least one lumen of said fitting member and having a distal end extending out from said distal end of said fitting member and connected to said conductor, and a proximal end exiting out from said pivotable post; and g. a slidable member including a slide block fitted into said longitudinal slot so that the walls of said longitudinal slot constrain the slide block to longitudinal movement between said proximal and distal ends of said rotatable housing with one longitudinally extending channel formed in the slide block for receiving and securing said proximal end of said rod therein, where holding said ratchet mechanism and rotating said rotatable housing can orient said cutting edge of said cutter member into a correct cutting position for cutting the patient's sphincter.

7. The sphincterotome device in accordance with claim 6 further comprising a heat shrink tubing for enclosing said proximal end of said tubular member and said distal end of said fitting member for providing strain relief.

8. The sphincterotome device in accordance with claim 6 further comprising indicating means at said distal end of said tubular member for providing visual indication of the position of said distal end of said tubular member in the patient.

9. The sphincterotome device in accordance with claim 6 further comprising first and second distal cylindrical tubes, where the first distal cylindrical tube is affixed within the interior of said tubular member and the second distal cylindrical tube is affixed within the interior of the first distal cylindrical tube, and located adjacent to said distal end for stabilizing and supporting said cutter member.

10. The sphincterotome device in accordance with claim 9 further comprising a proximal cylindrical tube affixed within the interior of said tubular member and remote from said first and second distal cylindrical tubes for also stabilizing and supporting said cutter member.

11. The sphincterotome device in accordance with claim 10 wherein said cutter member comprises a wire bowed between first and second locations at said distal end of said tubular member and located adjacent to said first and second distal cylindrical tubes and said proximal cylindrical tube.

12. The sphincterotome device in accordance with claim 6 wherein said tubular member has an opening at said distal end.

13. The sphincterotome device in accordance with claim 6 wherein said rotatable housing further comprises a thumb receiving member affixed to said distal end.

14. The sphincterotome device in accordance with claim 6 wherein said slidable member further comprises a pair of extending finger receiving members extending oppositely and transversely from said slide block.

15. The sphincterotome device in accordance with claim 6 wherein said tubular member being sized to be received in the lumen of the endoscope.

16. The sphincterotome device in accordance with claim 6 wherein said ratchet mechanism causes said rotatable housing to rotate such that said cutting member is approximately between the eleven o'clock position and one o'clock position for cutting the patient's sphincter.

17. A sphincterotome used in conjunction with an endoscope for cutting a patient's sphincter or like, comprising:

a. a tubular member having a proximal end and a distal end, the distal end extending into said endoscope and into engagement with the patient's sphincter;

b. a cutter member having a cutting edge located along said distal end of said tubular member, wherein the cutting edge is movable in a cutting plane to cut the patient's sphincter, the cutter member being connected to a conductor disposed in said tubular member;

c. a rotatable housing having a slot formed therein;

d. a ratchet mechanism attached between said rotatable housing and said proximal end of said tubular member, and having a pivotable post rotatably secured within said slot of said rotatable housing;

e. a rod movably disposed in said ratchet mechanism and having one end connected to said conductor; and f. a slidable member movably connected in said slot and having means for receiving and securing the other end of said rod therein, where holding said ratchet mechanism and rotating said rotatable housing can orient said cutting edge of said cutter member into a correct cutting position for cutting the patient's sphincter.

18. The sphincterotome in accordance with claim 17 further comprising a heat shrink tubing for enclosing said proximal end of said tubular member and partially enclosing said ratchet mechanism for providing strain relief.

19. The sphincterotome in accordance with claim 17 further comprising indicating means at said distal end of said tubular member for providing visual indication of the position of said distal end of said tubular member in the patient.

20. The sphincterotome in accordance with claim 17 further comprising first and second distal cylindrical tubes, where the first distal cylindrical tube is affixed within the interior of said tubular member and the second distal cylindrical tube is affixed within the interior of the first distal cylindrical tube and located adjacent said distal end of said tubular member for stabilizing and supporting said cutter member.

21. The sphincterotome in accordance with claim 20 further comprising a proximal cylindrical tube affixed within the interior of said tubular member and remote from said first and second distal cylindrical tubes for also stabilizing and supporting said cutter member.

22. The sphincterotome in accordance with claim 21 wherein said cutter member comprises a wire bowed between first and second locations and located adjacent to said first and second distal cylindrical tubes and said proximal cylindrical tube respectively.

23. The sphincterotome in accordance with claim 17 wherein said rotatable housing further comprises a thumb receiving member for receiving a user's thumb.

24. The sphincterotome in accordance with claim 17 wherein said slidable member further comprises a pair of extending finger receiving members extending oppositely and transversely for receiving the forefinger and index finger of the user's hand.

25. The sphincterotome in accordance with claim 17 wherein said tubular member being sized to be received in the lumen of the endoscope.

26. The sphincterotome device in accordance with claim 17 wherein said ratchet mechanism causes said rotatable housing to rotate such that said cutting member is approximately between the eleven o'clock position and one o'clock position for cutting the patient's sphincter.

27. A papillotome, comprising:

a. a tubular member having a proximal end and a distal end;

b. a cutter member having a cutting edge located along said distal end of said tubular member, wherein the cutting edge is movable in a cutting plane to cut a patient's muscle, the cutter member being connected to an electrical conductor disposed in said tubular member;

c. a ratchet mechanism attached to said proximal end of said tubular member;

d. a rod disposed in said ratchet mechanism and having one end connected to said electrical conductor;

e. means for rotatably retaining said ratchet mechanism, and means for receiving and securing the other end of said rod, where holding said ratchet mechanism and turning said rotatably retaining means can orient said cutter member in a correct angle for cutting the patient's muscle;

f. said cutter member comprising a wire bowed between first and second locations at said distal end of said tubular member; and g. first and second distal cylindrical tubes, where the first distal tube is affixed within the interior of said tubular member and the second distal tube is affixed within the interior of said first distal tube and located adjacent to said second location for stabilizing and supporting said cutter member.

28. The papillotome in accordance with claim 27 further comprising a heat shrink tubing for enclosing said proximal end of said tubular member.

29. The papillotome in accordance with claim 27 further comprising a proximal cylindrical tube affixed within the interior of said tubular member and located adjacent to said first location for also stabilizing and supporting said cutter member.

30. The papillotome in accordance with claim 27 wherein said means for receiving and securing the other end of said rod comprises a slidable member including a slide block fitted within said rotatably retaining means.

31. A method of surgically cutting a patient's sphincter, the method comprising the steps of:

a. positioning an endoscope near the patient's sphincter to allow viewing of the sphincter;

b. providing a sphincterotome device having a tubular member with a proximal end and a distal end;

c. inserting said distal end of said tubular member out of an opening of said endoscope and into engagement with the patient's sphincter;

d. longitudinally positioning a cutter member which has a cutting edge located along said distal end of said tubular member, wherein the cutting edge is movable in a cutting plane to cut the patient's sphincter, and connecting the cutter member to a conductor disposed in said tubular member;

e. providing a rotatable housing means having a longitudinal slot formed therein;

f. attaching a ratchet mechanism between said rotatable housing means and said proximal end of said tubular member, and rotatably securing a pivotable post to said rotatable housing means;

g. disposing a rod in said ratchet mechanism and connecting one end of the rod to said conductor;

h. slidably connecting a slidable member in said longitudinal slot to move in a longitudinal movement and providing means for receiving and securing the other end of said rod therein;

i. holding said ratchet mechanism and rotating said rotatable housing means which orients said cutting edge of said cutter member into a correct cutting position for cutting the patient's sphincter; and j. energizing said conductor with said cutter member with said cutting edge in said cutting plane to cut the sphincter radially outward of a center of the sphincter.

32. The method in accordance with claim 31 further comprising the step of heating a heat shrink tubing for enclosing said proximal end of said tubular member and partially enclosing said ratchet mechanism for providing strain relief.

33. The method in accordance with claim 31 further comprising the steps of providing indicating means at said distal end of said tubular member for providing visual indication of the position of said distal end of said tubular member in the patient.

34. The method in accordance with claim 31 further comprising the steps of attaching a first distal tube within the interior of said tubular member and a second distal tube within the first distal tube and located adjacent said distal end of said tubular member for stabilizing and retaining said cutter member.

35. The method in accordance with claim 34 further comprising the steps of attaching a proximal tube within the interior of said tubular member and remote from said first and second distal tubes for also stabilizing and supporting said cutter member.

36. The method in accordance with claim 34 further comprising the steps of forming a wire bowed between first and second locations on said tubular member and located adjacent to said proximal tube and said first and second distal tubes respectively.

37. A method of surgically cutting a patient's muscle, the method comprising the steps of:

a. positioning an endoscope near the patient's muscle to allow viewing of the muscle;

b. providing a papillotome having a tubular member;

c. inserting said tubular member out of an opening of said endoscope and into engagement with the muscle;

d. positioning a cutter member which has a cutting edge along a respective end of said tubular member, wherein the cutting edge is movable in a cutting plane to cut the patient's muscle;

e. attaching a ratchet mechanism to said respective end of said tubular member;

f. disposing a rod in said ratchet mechanism and connecting one end thereof to said cutter member;

g. holding said ratchet mechanism and rotating said rod which orients said cutting edge of said cutter member into a correct cutting position for cutting the patient's muscle; and h. energizing said cutter member with said cutting edge in said cutting plane to cut the muscle radially outward of a center of the muscle.

38. The method in accordance with claim 37 further comprising the steps of heating a heat shrink tubing for enclosing a respective end of said tubular member and a partially enclosing said ratchet mechanism for providing strain relief.

39. The method in accordance with claim 37 further comprising the steps of forming a wire bowed between first and second locations at said respective end of said tubular member.

40. The method in accordance with claim 37 further comprising the steps of attaching a first tube within the interior of said tubular member and a second tube within the first tube and located adjacent to said respective end of said tubular member for stabilizing and retaining said cutter member.

41. The method in accordance with claim 40 further comprising the steps of attaching a third tube within the interior of said tubular member and remote from said first and second tubes for also stabilizing and supporting said cutter member.

* * * * *